United States Patent [19]

McKague et al.

[11] 3,992,452
[45] Nov. 16, 1976

[54] METHOD FOR THE PRODUCTION OF ALKOXYCYCLOHEXANONES

[75] Inventors: Allan B. McKague, Vancouver; William deWaal, Richmond; Carl E. Van Winckel, West Vancouver, all of Canada

[73] Assignee: CPC International, Inc., Englewood Cliffs, N.J.

[22] Filed: Apr. 26, 1974

[21] Appl. No.: 464,554

Related U.S. Application Data

[60] Division of Ser. No. 251,132, May 8, 1972, Pat. No. 3,819,719, which is a continuation-in-part of Ser. No. 233,795, March 10, 1972, abandoned, which is a continuation-in-part of Ser. No. 124,449, March 15, 1971, abandoned.

[52] U.S. Cl. .............................................. 260/586 R
[51] Int. Cl.² .................. C07C 45/00; C07C 41/10
[58] Field of Search ............................... 260/586 R

[56] References Cited
OTHER PUBLICATIONS

Durbeck et al., "Tetrahedron" vol. 27, pp. 2927–37 (1971).

*Primary Examiner*—Norman Morgenstern
*Attorney, Agent, or Firm*—Seed, Berry, Vernon & Baynham

[57] ABSTRACT

Alkoxy phenols such as o-methoxyphenol (guaiacol) and o-ethoxyphenol are prepared from substituted cycloaliphatic ketones by dehydrogenation thereof in the presence of a Group VIII noble metal catalyst, preferably palladium supported on carbon, at a temperature of 150° to 250° C. The reaction is carried out neat or in the liquid phase using an alicyclic ester reaction solvent having a boiling point ranging from about 150° to 250° C. The substituted cycloaliphatic ketone reactant, such as 2-chlorocyclohexanone is prepared by chlorination of cyclohexanone with subsequent conversion of the 2-chlorocyclohexanone to the alkoxycyclohexanone compound which is dehydrogenated.

6 Claims, No Drawings

METHOD FOR THE PRODUCTION OF ALKOXYCYCLOHEXANONES

CROSS REFERENCE TO RELATED APPLICATION

This application is a division of application Ser. No. 251,132, filed May 8, 1972, now U.S. Pat. No. 3,819,719 which is a continuation-in-part application of Ser. No. 233,795, filed Mar. 10, 1972, entitled "Production of Guaiacol", now abandoned which is a continuation-in-part of application Ser. No. 124,449, filed Mar. 15, 1971, "Production of Hydroxy-aromatic Compounds by Catalytic Dehydrogenation of Substituted Cycloaliphatic Ketones", now abandoned.

BACKGROUND OF THE INVENTION

1. Field of the Invention

This invention relates to a process for the preparation of o-alkoxyphenols from substituted cycloaliphatic compounds, such as 2-chlorocyclohexanone, by conversion of the chloroketone to the alkoxyketone and dehydrogenation thereof by contact with a Group VIII noble metal catalyst.

2. Prior Art Relating to the Disclosure

O-methoxyphenol (guaiacol) and o-ethoxyphenol have many uses as intermediates in organic synthesis, O-methoxyphenol is also useful as a reagent in detecting lignin and, medicinally as an antiseptic.

It is known that alicyclic ketones dehydrogenate to phenols by catalytic means as described, for example, in the following U.S. Pat. Nos. 2,321,551; 2,503,641; 2,588,359; 2,628,985; 2,708,208; 3,256,348; 3,345,382; 3,358;044; 3,391,199; 3,514,492; and 3,534,110. It is also known that cyclohexanediols can be catalytically dehydrogenated to yield phenol and pyrocatechol Catalytic dehydrogenation of 2-hydroxycyclohexanone or cyclohexane, 1, 2-dione in the liquid phase to pyrocatechol by contact with a noble metal catalyst is described in Belgian patent No. 763,803.

Preparation of 2-methoxy-cyclohexanone from 2-hydroxycyclohexanone is reported in the literature; M. Bergmans and M. Gierth, Ann. 448, 48(1926) and H. W. Durbeck, C. G. B. Frishkorn and K. Hilpert, Tetrahedron 27,2927 (1971).

SUMMARY OF THE INVENTION

This invention relates to a process for the preparation of o-alkoxyphenols by dehydrogenation of the corresponding alkoxy-cyclohexanone with a Group VIII noble metal catalyst at a temperature range from about 150° to 250° C. Certain of the objects of this invention are: (1) to provide a process for the production of o-alkoxyphenols from the corresponding alkoxy-cyclohexanone by contact with a Group VIII noble metal catalyst at a temperature of 150° to 250° C; (2) to provide a process for production of o-methoxyphenol or o-ethoxyphenol by contact with a Group VIII noble metal catalyst in high yield, high reaction rate and minimal degradation of catalyst, the reaction carried out neat or in an alicyclic ester reaction solvent at a temperature of from about 150° to 250° C; (3) to provide a process for the production of o-methoxyphenol from 2-methoxy-cyclohexanone derived from 2-chlorocyclohexanone; and (4) to provide a process for the production of 2-methoxy- or 2-ethoxycyclohexanone from 2-chloro-cyclohexanone in relatively high yield at low cost.

DESCRIPTION OF THE PREFERRED EMBODIMENTS

The starting material for production of the alkoxyphenol is the corresponding alkoxy-cyclohexanone which is prepared by chlorination of cyclohexanone followed by conversion to the corresponding alkoxy-cyclohexanone as indicated below:

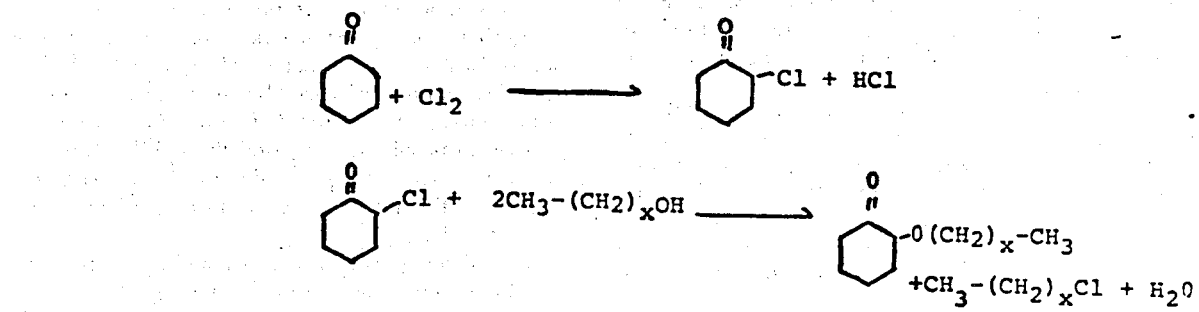

where $x = 0$ or $1$

It has been found that 2-chlorocyclohexanone can be converted to the corresponding alkoxy-cyclohexanone by procedures which are economical, give superior yields, and can be carried out more easily than by known reported methods. 2-chlorocyclohexanone prepared by chlorination of cyclohexanone, is dissolved in an excess of a monohydric alkyl alcohol having 1 to 2 carbon atoms and heated in a closed vessel to a temperature of from about 110° to 220° C., preferably from about 125° to 200° C. for a time ranging from 5 minutes to 6 hours. The concentration of the chlorocyclohexanone in the alkyl alcohol can be varied widely, for example, from 2 to 20 or more moles alcohol per mole of chloroketone. After reaction the excess alcohol is removed by distillation and the residue containing the alkoxy-cyclohexanone recovered by extraction with an appropriate solvent which allows isolation of the alkoxy-cyclohexanone, such as water or methylene chloride. The reaction vessel should be corrosion resistant, i.e., glass-lined or a suitable stainless steel alloy. Low boiling side reaction products include the corresponding alkyl chloride and dialkyl ether which are separated from the alkoxyketone by suitable methods. Yields of the alkoxyketone of greater than 90% are obtained.

It has also been found that the alkyl chloride byproduct can be eliminated by the removal of the hydrogen chloride as it is formed. This can be accomplished by the addition of a basic substance having a pH ranging from 7–11 such as tertiary amine (trimethyl- or triethylamine), inorganic alkali or alkaline earth carbonate (calcium carbonate or sodium carbonate), or alkaline earth oxide such as MgO or CaO to the reaction mass. The amount of basic material added should be in the range of from about 1.0 to 1.05 equivalents per mole 2-chlorocyclohexanone.

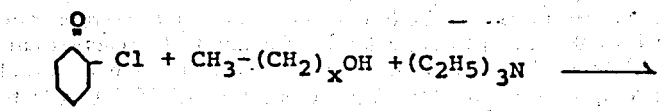

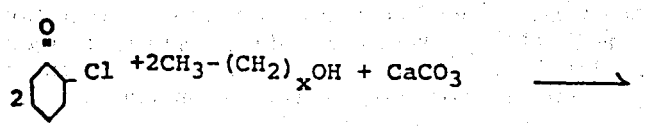

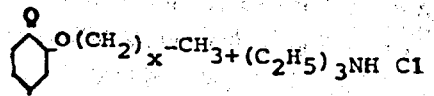

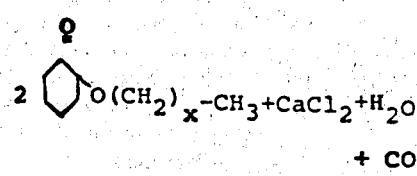

where $X = 0$ or $1$

The amine reacts with HCl to form the hydrochloride. The amine is easily separated from the alkoxy-cyclohexanone for recovery and reuse. Removal of the HCl during the reaction can also be accomplished by reacting the chloroketone with the alkyl alcohol in the presence of calcium carbonate. After removal of the alcohol the calcium chloride can be removed by precipitation or water may be added and the product extracted with an organic solvent.

Catalytic dehydrogenation of the alkoxy-cyclohexanone may be carried out in the vapor or liquid phase but preferably in the liquid phase neat or by using polar solvents boiling in the range of 150° to 250° C. Catalytic dehydrogenation carried out on the alkoxy-cyclohexanone neat gives surprisingly high conversion with little or no catalyst contamination and few side reaction products.

The catalysts used in this process are Group VIII noble metal compounds such as palladium, platinum and rhodium. Preferably palladium supported on an inert carrier such as carbon is used, although other types of inert supports such as barium sulfate may be used. The amount of palladium relative to the cycloketone reactant may be varied from about 0.10 to 3.0 wt. %, 0.20 wt. % being preferred. Greater amounts than this do not appear to have any appreciable advantage.

The dehydrogenation liquid phase reaction is carried out by mechanical agitation and refluxing of the alkoxy-cycloketone reactant with the catalyst in an alicyclic ester solvent having a boiling range of from 150° to 250° C. and preferably from 175° to 215° C. at atmospheric or superatmospheric pressures. Temperatures much below 150° C. give a slow rate of reaction while temperatures above about 250° C., while giving a faster reaction rate in certain cases, do not necessarily increase the yield and may result in undesired reactions.

Ester reaction solvents preferred for the liquid phase reaction include: ethylene glycol diacetate, tri-methylene glycol diacetate, propylene glycol diacetate, 2,3-butane diol diacetate, diisopropyl succinate, and dimethyl succinate. The preferred solvents are cyclohexyl esters such as cyclohexylacetate or cyclohexylpropionate. The ratio of solvent to alkoxy-cycloketone may be varied from 0–30:1. Preferably, a ratio of at least 5:1 solvent to alkoxy-cycloketone is employed as a smaller ratio produces increased amounts of undesired side reaction products. Refluxing the alkoxy-cycloketone with the catalyst in the ester solvent is continued until evolution of hydrogen has reached 75 – 95% of theory. The time of reaction is dependent upon the temperature and other factors and generally ranges between 20 minutes to four hours. After reaction the solvent and reaction products are fractionated either directly or by first forming the sodium salt of the alkoxyphenol with an aqueous sodium hydroxide solution and then distilling the water and ester solvent. The salt is then acidified and the alkoxyphenol isolated with resulting yields of greater than 70%.

When carrying the dehydrogenation out neat, the alkoxycyclohexanone is refluxed over the catalyst at atmospheric or superatmospheric pressure until evolution of hydrogen has reached 75–95% of theory. The rate of reaction is increased by an increase in pressure. For example, it was noted that a pressure increase by 9 psi over atmospheric increased the reaction rate by a factor of 2. The catalyst can be reused for several runs without addition of fresh catalyst or significant loss of catalyst activity.

The following examples are exemplary of the invention but are not to be considered limiting of the specification and claims in any way.

EXAMPLE 1

A solution of 2-methoxycyclohexanone (5.0 g), in trimethylene glycol diacetate (50 ml) was refluxed with stirring with 5% palladium on charcoal (1.0 g) until 75% of the theoretical amount of hydrogen had evolved (about one hour). After cooling the catalyst was filtered and the colorless filtrate shown to contain o-methoxyphenol by gas chromatography and thin layer chromatography. A yield in the range of 75% was estimated by gas chromatographic comparison with standard solutions of o-methoxyphenol by gas chromatography.

EXAMPLE 2

In a vessel equipped with an efficient stirrer a solution of 10 gm. 2-methoxycyclohexanone in 100 ml cyclohexylpropionate was refluxed over 400 mg. of 5% palladium on carbon until approximately 75% hydrogen had evolved (approximately one hour). The catalyst was removed by filtration. Analysis of the product by gas chromatography indicated a selectivity to o-methoxyphenol of 93–98%.

EXAMPLE 3

Dehydrogenations of 2-methoxycyclohexanone were carried out as in Example 2 with the exception of the reaction solvents. Cyclohexylacetate and diisopropylbenzene were used. Reaction times (based on approximately 75% hydrogen evolution) were 2.5 hours and 6 hours respectively. The reaction time using cyclohexylacetate was substantially decreased by carrying out the reaction at 5 psi.

EXAMPLE 4

2-methoxycyclohexanone was prepared by dissolving 30 gm. 2-chlorocyclohexanone in 160 ml. methanol and heating the solution in a sealed vessel at 125° C. for approximately four hours. The reaction mass was then cooled and the methanol removed by distillation at reduced pressure. After most of the methanol was distilled off, the residue containing the 2-methoxycyclohexanone was diluted with methylene chloride and extracted with an aqueous solution of sodium hydroxide. After distillation a yield of 90–95% 2-methoxycyclohexanone was obtained.

EXAMPLE 5

2-methoxycyclohexanone was prepared as in Example 4, by dissolving 98 gm. 2-chlorocyclohexanone in 750 ml. methanol and heating the solution in a sealed vessel at 160° C. for 15 minutes. The conversion was 98–99% with a yield of greater than 90%.

EXAMPLE 6

A solution of 149 gm. 2-chlorocyclohexanone, 116 gm. triethylamine, and 338 ml methanol was heated in a sealed vessel at 190° C. for 15 minutes. After cooling, the methanol was distilled off at atmospheric pressure, using a mechanical stirrer. The residue containing 2-methoxycyclohexanone was diluted with water and a small excess of aqueous sodium hydroxide solution added. The 2-methoxycyclohexanone was extracted and the extract distilled. The yield of 2-methoxycyclohexanone was 76–79% with high recovery of the triethylamine for reuse.

EXAMPLE 7

2-methoxycyclohexanone was prepared as in Example 6 except that diethylether was added to the reaction mass after removal of the methanol by distillation. The suspension was filtered, the filtrate concentrated and the residual oil phase distilled to afford an 89% yield of 2-methoxycyclohexanone.

EXAMPLE 8

2-methoxycyclohexanone was prepared by dissolving 132 gm. 2-chlorocyclohexanone in 600 ml. of methanol in the presence of 50 gm. calcium carbonate and heating the suspension at 160° C. for 15–20 minutes. After removal of the methanol, the calcium chloride was precipitated by the addition of methylene chloride to the residual material. The calcium chloride was removed by filtration and the filtrate was distilled to yield an 80–85% yield of 2-methoxycyclohexanone.

EXAMPLE 9

A suspension of 800 mg. of 5% palladium on charcoal (half of which has been used for a previous dehydrogenation) in 100 gm. of distilled 2-methoxycyclohexanone was stirred and refluxed under a pressure of 9 psi. After 5 hours approximately 75% of the ketone was converted. The reaction was stopped and the crude product separated by filtration. Distillation afforded a high yield of o-methoxyphenol with virtually no residue in the still pot. The catalyst can be reused with no additional fresh catalyst added.

EXAMPLE 10

2-ethoxycyclohexanone was prepared in 97% yield by heating 2-chlorocyclohexanone with an excess of ethyl alcohol at 190° C. in a sealed reactor. 1.0 gm. of distilled 2-chlorocyclohexanone and 16 ml. of anhydrous ethyl alcohol were heated at 190° C. for one-half hour in a sealed glass-lined stainless steel reactor. Analysis of the cooled reaction mixture showed 97% conversion of 2-chlorocyclohexanone to 2-ethoxycyclohexanone.

EXAMPLE 11

A solution of 10 gm. 2-ethoxycyclohexanone in 100 ml. cyclohexylpropionate was refluxed over 400 mg. of palladium on carbon until approximately 75% hydrogen had evolved. The catalyst was removed by filtration. O-ethoxyphenol was obtained in high yield.

The embodiments of the invention in which a particular property or privilege is claimed are defined as follows:

1. A process for the preparation of an alkoxycyclohexanone selected from the group consisting of 2-methoxy and 2-ethoxycyclohexanone in high yield, comprising:
  heating a reaction mass consisting essentially of 2-chlorocyclohexanone dissolved in an excess of a monohydric alkyl alcohol having 1 or 2 carbon atoms in a closed vessel to a temperature of from 110° to 200° C. to yield the corresponding alkoxycyclohexanone and hydrogen chloride,
  removing excess alcohol from the reaction mass, and
  recovering the alkoxycyclohexanone from the reaction mass.

2. The process of claim 1 wherein 2–20 moles of alcohol are used per mole of 2-chlorocyclohexanone.

3. The process of claim 1 wherein the reaction mass includes a basic substance selected from the group consisting of tertiary amines, alkali and alkaline earth oxides having a pH ranging from 7–11, the basic substance reacting with the hydrogen chloride as it is formed to form the corresponding chloride salt.

4. The process of claim 3 wherein the basic substance is an organic tertiary amine.

5. The process of claim 3 wherein the basic substance is an alkali or alkaline earth carbonate.

6. The process of claim 3 wherein the basic substance is an alkaline earth oxide.